United States Patent
Olsson

(10) Patent No.: US 6,937,400 B2
(45) Date of Patent: Aug. 30, 2005

(54) METHOD AND DEVICE FOR IMAGE DISPLAY

(75) Inventor: Kent Olsson, Stockholm (SE)

(73) Assignee: CK Management AB, Stockholm (SE)

( * ) Notice: Subject to any disclaimer, the term of this patent is extended or adjusted under 35 U.S.C. 154(b) by 0 days.

(21) Appl. No.: 10/484,769

(22) PCT Filed: Jul. 23, 2002

(86) PCT No.: PCT/SE02/01407

§ 371 (c)(1),
(2), (4) Date: Jan. 23, 2004

(87) PCT Pub. No.: WO03/010977

PCT Pub. Date: Feb. 6, 2003

(65) Prior Publication Data

US 2004/0174605 A1 Sep. 9, 2004

(30) Foreign Application Priority Data

Jul. 23, 2001 (SE) .............................. 0102584

(51) Int. Cl.⁷ .............................. G02B 27/14
(52) U.S. Cl. ..................... 359/630; 359/462; 345/7; 345/8; 348/115; 362/103
(58) Field of Search ............... 359/462, 464, 359/466, 473, 475, 477, 630–633; 345/7–9; 348/115; 362/103; 600/109, 166, 160, 475, 477

(56) References Cited

U.S. PATENT DOCUMENTS 5,682,173 A * 10/1997 Holakovszky et al. ......... 345/8
6,157,291 A * 12/2000 Kuenster et al. ............... 345/8
6,356,392 B1 * 3/2002 Spitzer ....................... 359/630

OTHER PUBLICATIONS

Personal Monitor from ALBACOMP (1997) (manufactor's site). Retrieved on Sep. 23, 2002 from the Internet: http://www.adeptmedicalconcepts.com/PersonalMonitor/main.htm —All documents: p. 1 "introduction", p. 2 "description", p. 3 "lectures", p. 4 "the sight we see". Claims 2,3 and 11: see p. 3, line 3.
PC Glasstron PLM–S700, SONY (1998) (manufactor's site). Retrieved on Sep. 23, 2002 from the Internet: http://sonystyle.com/pdfs/3862917111.pdf —See p. 12.
PCTV–K180 from Tek Gear HMD (1999) (manufactor's site). Retrieved on Apr. 18, 2002 from the Internet: http://www.tekgear.ca/ —See p. 1, line 2; p. 2, lines 1–3; all figures on p. 2.

* cited by examiner

Primary Examiner—Hung Xuan Dang
Assistant Examiner—Joseph Martinez
(74) Attorney, Agent, or Firm—Young & Thompson

(57) ABSTRACT

An object (3) is imaged and, after image processing, an image is displayed on a head-mounted display (10) in front of the eyes of a user of the display. The display (10) is constructed with two display modules (13, 14) for displaying the image, designed to be positioned in front of each eye within a limited section of each eye's field of vision, the display modules being arranged each to show a separate image and being designed to leave the field of view free towards the surroundings at least downwards and to the sides of the user. The display modules (13, 14) are advantageously arranged to show two different images, one in front of each eye, so that the user experiences a stereoscopic image with a perception of depth in a part of his field of vision at a predetermined distance in front of his eyes.

11 Claims, 2 Drawing Sheets

METHOD AND DEVICE FOR IMAGE DISPLAY

TECHNICAL FIELD

The invention relates to a method for image display and a device for image display.

KNOWN TECHNOLOGY

In normal open surgical operations, the surgeon views the site of the operation directly with his eyes and can therefore carry out various actions with good precision using his normal stereoscopic vision. It is, however, becoming increasingly common to use closed surgery techniques where the operation is carried out inside the body via only a small external incision. This makes it difficult for the surgeon to obtain a good view of the site of the operation. In order to solve this problem, the technique has been utilized of inserting an endoscope to the site of the operation and of obtaining by means of this an image on a display screen that can be viewed by the surgeon. This type of imaging has, however, the disadvantage that it does not provide any depth information, and in addition the image is displaced from the site of the operation, with the result that the surgeon finds it difficult to work with the required precision.

Attempts have been made to achieve stereoscopic imaging with images taken a certain distance apart and displayed with a certain displacement on a monitor, special 3D spectacles being used to look at the monitor and in this way to experience a perception of depth in the image. This type of solution has, however, proved to be difficult to use and tiring for the surgeon, particularly during operations that take a long time.

In order to give the surgeon a more comfortable working position and to allow his head to be directed towards the site of the operation the whole time, there have also been attempts to use a head-mounted image display device. Such equipment has, however, been found to be relatively heavy and therefore uncomfortable to use, and has, in addition, the disadvantage of hiding the surroundings to a considerable extent, with consequent difficulty for the user in orienting himself in the environs of the operation. In turn, this has, in addition to causing neck ache, back problems, eye fatigue and the like, often resulted in seasickness-like sensations for the user, with resultant problems in carrying out precision work.

Against this background, there is a clear need for new and better solutions within this field.

OBJECTS OF THE INVENTION

The object of the invention is to make it possible for, for example, a surgeon to obtain a better visual perception of a hidden operation site than has previously been possible, while at the same time making it possible for him to perceive the surroundings, particularly his own hands and the instruments that are used for the operation. Another object is that the solution must be restful for the user by having good optical properties and must be simple to use. An additional object is to achieve a head-mounted device that does not feel heavy and that is easy to adapt to fit different individuals.

DESCRIPTION OF THE INVENTION

These objects are achieved according to the invention by use of a method that has the characteristics described in claim 1 and also by means of a device that has the characteristics described in claim 10.

By using head-mounted equipment, where an image is projected in front of each eye, it is possible to create a perception of depth in the image, with the image at the required distance in front of the eyes. By also letting each of these image display positions take up a relatively limited part of the user's total field of vision, it is possible to achieve a free view both above and below the equipment and to the sides, which contributes to a great extent to allowing the user to retain a good orientation in the space where the equipment is used, which is particularly important during prolonged periods of work.

In addition, according to the invention, equipment is obtained that is easy to adapt to fit different individuals by changing one or more components, without all the other equipment needing to be changed. Each user can, for example, use his own equipment which is specially adapted for his own vision, which equipment can easily be supplemented by additional equipment for a special work situation.

On account of the heavy part of the equipment being worn at, for example, the user's hip-height, the weight of the head-mounted part of the equipment can be made low, which gives the user increased freedom of movement and feels comfortable, particularly in prolonged use. In this connection, it is, however, desirable that, as a result of the further development of components, the equipment can be made so light that the whole unit can be mounted on the head.

Electronic image processing makes it possible to control the image shown without changing the optical equipment by selecting a particular image-processing program for image processing and an image result that is particularly suited for a particular work situation. Thus, for example, the focus can be changed to a certain extent by electronic means, as can also, for example, the light intensity and the contrast. It is also possible to store required image types in a simple way by electronic means and to retrieve these for use out of a memory. In a corresponding way, for example, suitable settings for different work environments and lighting conditions can be stored and retrieved quickly out of a memory.

It will also be possible by electronic means to display temporarily other information to the user when required, for example X-ray images, images generated by magnetic cameras, medical records, etc, and after utilizing such information to return to the actual working situation.

The solution according to the invention also makes it possible, by the addition of one or more pieces of equipment or one or more monitors, to show a working situation experienced by a surgeon during an operation, something that is valuable for, for example, training purposes.

Additional characteristics and advantages are apparent from the following description and patent claims.

The invention will be described in the following in greater detail with reference to the embodiments shown in the attached drawings.

DESCRIPTION OF AN EMBODIMENT

Figure 1:
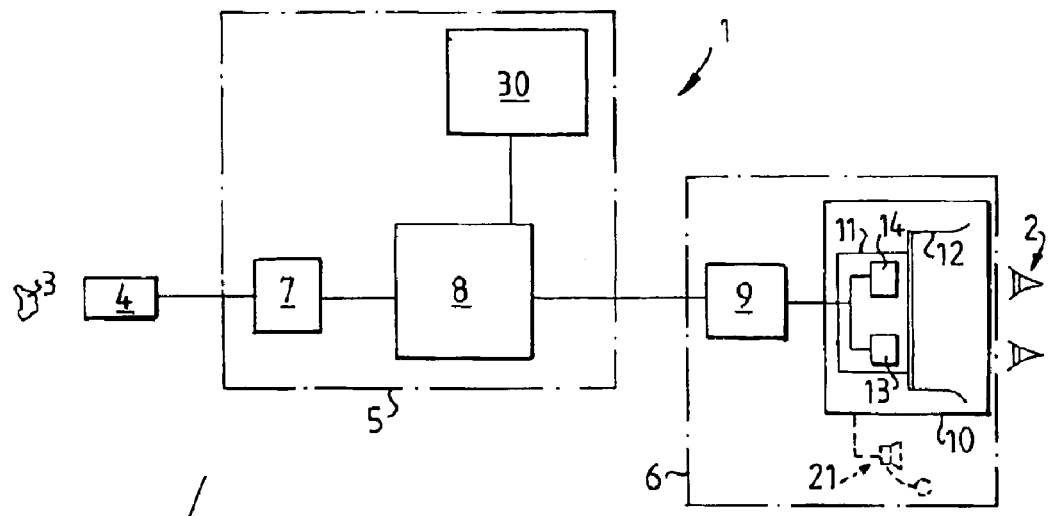
FIG. 1 shows a block diagram of a device for image display according to the invention.

FIG. 1 shows schematically a block diagram of a device 1 for image display constructed according to the invention, using which a user 2 can view an object 3, which is normally hidden from the user. The user 2 can, for example, be a surgeon who needs to view an internal organ in a human body in connection with carrying out an operation by closed surgery, that is the operation is carried out inside the patient without the surgeon being able to see the site of the operation directly. In this instance, the object 3, or the site of the operation, can be viewed using an endoscope 4 inserted inside the patient, which transmits light signals to an image-processing device 5, which is connected to an image-viewing device 6 worn by the user 2, via which the user 2 can see the object 3 with both eyes.

The light signals transmitted from the endoscope 4 are taken to a camera 7, which converts the light signals into electrical signals representing images of the object 3. From the camera 7 the signals are taken to a computer 8 in which suitable signal processing is carried out, and in which it is possible to control the signal processing in various ways, according to the need in different situations. Using a monitor 30 connected to the computer 8, it is possible to monitor visually different settings and image results. Together with the camera 7, the computer 8 can advantageously be designed to process an image base that is intended for the display of stereoscopic images to the user. The monitor 30 is normally not suited or intended for viewing this type of image, but is intended for the display of two-dimensional images. If so required, the camera 7 and the computer 8 can, of course, also display two-dimensional images.

By means of a suitable interface, signals are transmitted from the computer 8 to the image-viewing device 6, where the signals first reach a driver unit 9 and then, after processing in this, they reach a display 10, which comprises a display unit 11 which is intended to be attached to a holder 12, which is intended to be worn by the user 2 in a corresponding way to spectacles. The display unit 11 is in turn divided into two different display modules 13 and 14, one for each of the user's eyes. By, for example, imaging the object 3 stereoscopically using the endoscope 4, it is possible, after suitable image processing in the control unit 7, the computer 8 and the driver unit 9, to display different images in the two display modules 13, 14, so that the user 2 experiences a perception of depth in the image of the object 3 that is displayed via the two display modules 13, 14 as a result of stereoscopic vision. In this connection, it is desirable for the user to experience that the virtual object that is displayed in front of his eyes is at essentially the same distance as the real object, and that the focal distance of the virtual image is thus at a predetermined distance from the user, that is within the normal working distance for the user, the surgeon. Alternatively, a normal two-dimensional depiction can be selected.

Figure 2:
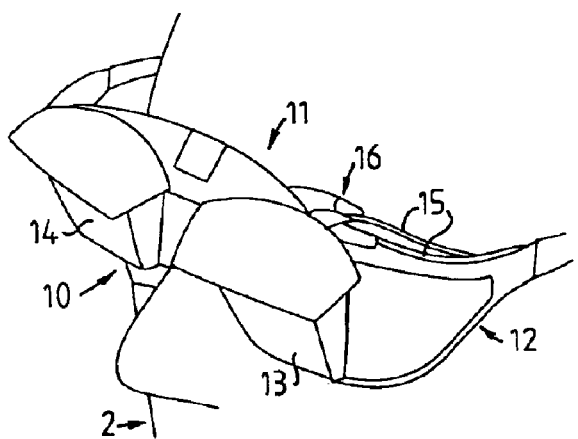
FIG. 2 shows a perspective view of a head-mounted display according to the invention.
Figure 3:
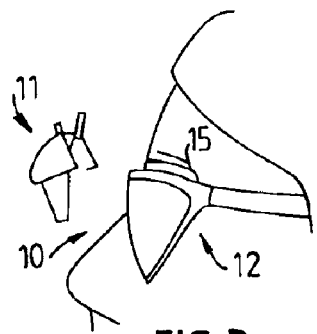
FIG. 3 shows a side view of the display in FIG. 2, partially dismantled.

The design of the display 10 is shown in greater detail in FIGS. 2 and 3. The holder 12 is suitably designed as a pair of protective spectacles, intended to protect the user's eyes, and these protective spectacles are advantageously optically adapted to the wearer. The optical adaptation can, for example, be ground into the spectacle lenses themselves or can comprise a special addition that is mounted on the spectacles, suitably on the inside. Each user has thus suitably his own individual holder 12. In FIG. 2, the display 10 is shown ready for use, with the display unit 11 attached to the holder 12, so that the display modules 13, 14 are each located in front of one of the user's eyes. In FIG. 3, the display unit 11 is shown removed from the holder 12. By attaching display units 11 that are adapted for different vision requirements, for example for close work or for micro-work, onto the holder 12, it is possible in a simple way to adapt the user's vision to the intended work situation as required. To make an electrical connection between the display unit 11 and the driver unit 9, which is suitably worn at the user's 2 waist height according to FIG. 6, the holder 12 has one or more leads 15, which can be connected to the display unit 11 via a connector 16 mounted partly on the holder 12 and partly on the display unit 11. This connector 16 can be designed in a number of ways, as required, in order to provide individual connection of the display modules 13 and 14 to the driver unit 9.

As also shown in FIGS. 2 and 3, the display unit 11 is so designed that the display modules 13 and 14 only partially obscure the user's 2 vision and thus allow the user to see freely to the sides of the display unit 11 and below and above it. This is essential to enable the user to see his hands and the instruments that are being used, and to provide a good orientation and sense of space in the area where the work is being carried out, particularly during long periods of work. The ability to see up and down counteracts the danger of the user feeling queasy or seasick. In addition, according to the invention, the display 10, that is the combination of the display unit 11 and the holder 12, has a low weight, suitably less than 100 g, which means that the strain on the neck and back is not perceived as troublesome. In addition, the electrical energy consumption of the equipment is low, which means that a troublesome temperature problem does not arise.

Figure 4:
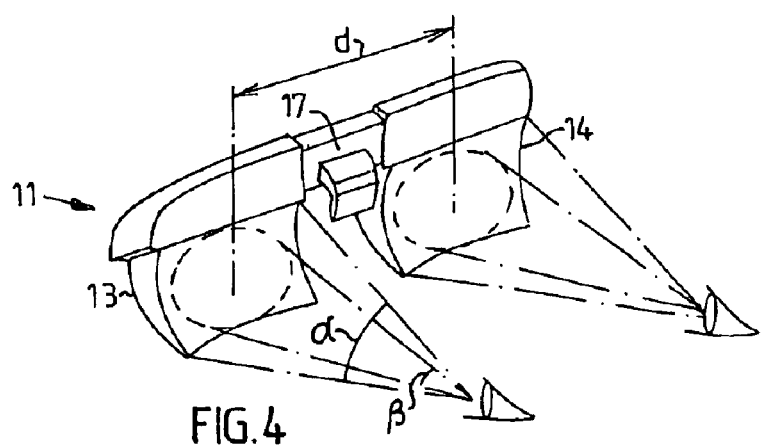
FIG. 4 shows a perspective view of a display module seen obliquely from the back.
Figure 5:
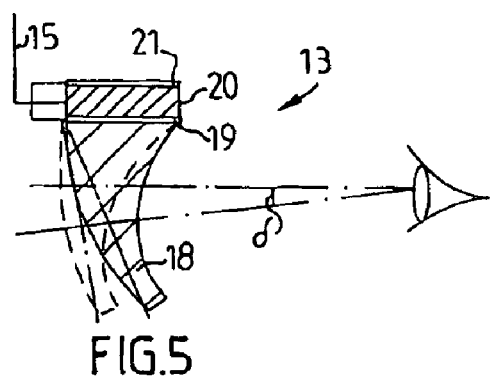
FIG. 5 shows a vertical section through a unit in a display module.

The construction of the display unit 11 is shown in greater detail in FIGS. 4 and 5. FIG. 4 shows that the two display modules 13 and 14 are supported on a joint fixing 17 designed to be attached to the holder 12, which fixing 17 suitably allows displacement of the two display modules 13 and 14 in order to match their distance apart to the interpupillary distance d of the user, in order to provide optimal vision. It is also shown that the two display modules 13 and 14, viewed from the user, are essentially rectangular, for example with a larger width than height. The size is such that the user can see the diagonal within an angle $\alpha$ of at most approximately 50°, suitably approximately 30°. The circular image that can be viewed should be able to take up an angle $\beta$ of at least approximately 15°, suitably approximately 25°. The two images displayed must in addition have the property that they give the user the impression that the viewed object 3 is located at the intended working distance, for example approximately 0.2–1.2 m from the eyes. For seated work, a suitable distance is approximately 0.4 m, while for standing work a suitable distance is 0.6–0.8 m, that is at an arm's length. For microscopy, on the other hand, a suitable distance can be as small as approximately 0.2 m.

FIG. 5 shows a vertical section through a display module 13, the corresponding construction applying for the other display module 14. The user sees the displayed image in a specially-designed prism 18, and his perception is that the displayed object lies beyond the prism, where his gaze is directed. The image is generated electronically by means of an essentially horizontally-placed image screen 19, suitably of the LCD type, above the prism 18, which is illuminated from the back by means of a light source 20 and can be viewed via the prism 18. To enable good viewing in daylight, it is therefore important to be able to set suitable contrast and light intensity. In order to clearly delimit the image field from the surroundings, there is a frame, for example a dark frame, around the image field. An electronic circuit 21 intended for controlling the image screen 19 is located above the light source 20. The abovementioned parts are suitably protected by a cover of lightweight material not shown in this figure in greater detail. By this means, a compact and lightweight construction is obtained for the display module 13, where the prism 18 can be of glass or suitably of other material.

A lead 15 connects the display module to the driver unit 9 for the transmission of electrical signals and electrical energy. In order to make possible restful vision with relaxed eye muscles for the user, the display module 13 is suitably located according to FIG. 5 in such a way that the user can have his gaze directed slightly downwards at an angle of $\delta$ relative to the horizontal plane. The size of this angle $\delta$ should suitably be in the range of approximately 2–12° and can advantageously be approximately 5–9°. In order to make possible good individual adaptation for different users, in addition to the abovementioned setting of the interpupillary distance, it is suitably also possible to make other adjustments to suit other physical characteristics of the user. Thus, for example, the adaptation for different users can be achieved by making the fixing 17 between the display unit 11 and the holder 12 adjustable in various respects. This makes it possible, for example, to rotate the display unit 11 around a horizontal axis with its centre at the pupil, by the whole display unit 11 being mounted in such a way that it can rotate relative to the holder 12 by making it movable in a vertical direction along a suitably curved track at the fixing 17. By this means, the viewing direction can be changed in the vertical direction, for example from approximately 10° above the horizontal line to approximately 10° below the horizontal line. In addition, by making the fixing 17 so that it allows the distance from the display unit 11 to the user's eye to be changed, it is possible, in combination with the adaptation to the user's interpupillary distance, to achieve a good individual fit between the user and the display unit.

In order to achieve a good individual adaptation of the prism 18, the surface of this facing towards the eye should have a shape that corresponds to the shape of the viewer's eye. As the eye has normally a larger radius of curvature viewed in the horizontal plane than in the vertical plane, the prism should thus have a corresponding curvature of the surface facing the eye, with the curved surfaces of the eye and the prism, viewed in the horizontal plane and the vertical plane, having essentially the same centres of curvature. This means that users with different sizes of eyes should have individually adjusted display units in order to achieve optimal vision. By making the prism 18 adjustable relative to the eye, the prism can be given the best location for the wearer in question. In this respect, it is desirable that for good adaptation for different eyes either the prism or the display unit should be able to be rotated slightly in a sideways direction so that the correct position can be set with regard to the geometry of the eye in question, in particular the location of the macula in the eye.

The electronic image processing makes it possible by means of a suitable image-processing program, adapted to the hardware concerned, to manipulate in a number of different ways the image that the user will see. It is, for example, simple to change colours, contrast and light intensity in the image as required, suitably via operating controls on the driver unit 9. By this means, suitable changes can be made while the work is in progress, as required. It is also possible to use a number of previously determined combinations of different parameters and to select between these combinations as required. Another possibility is to manipulate the image by means of suitable software so that it appears to the user that it is moved closer or further away, for example for better viewing of details or for a better overview. The electronic image processing also makes it possible to adapt different types of peripheral equipment, such as monitors and display equipment, to each other easily.

Figure 6:
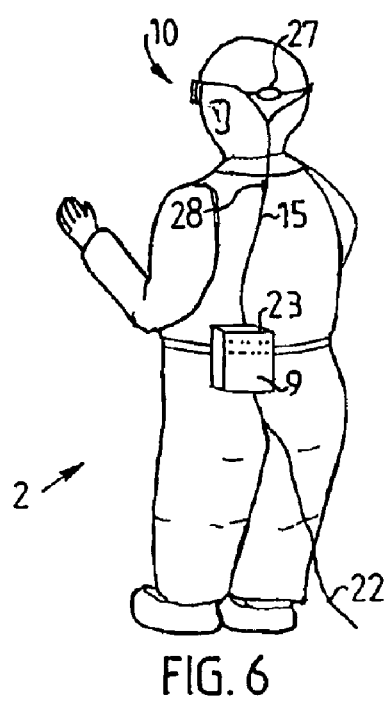
FIG. 6 shows a user of a device according to the invention.

The image-viewing device 6 shown, can, according to FIG. 1, also be provided with a sound installation 21 that gives the user the possibility of acoustic communication, voice control or the like. For this purpose, a microphone of the conduction type can, for example, be incorporated into an arm on the holder 12 which is shaped as a spectacle frame and can thereby be in contact with the user's skull, while the loudspeaker consists of an ear piece fitted to the user's ear. In FIG. 6, the user 2 is shown to be connected to the image-processing device 5 by a lead 22 for the transmission of signals and energy, but it is of course within the scope of the invention to place the requisite energy supply in the form of batteries in the driver unit 9 instead and to utilize wireless signal transmission to the image-processing device 5 and any other devices. Nor is there anything preventing, for example, more than one image-viewing device 6 being connected to the image-processing device 5, which, if required, can also be provided with more than one monitor 30.

By providing the equipment with a movement sensor that detects movement of the user's head, it is possible to move the image in relation to the user's eyes as the head moves.

Each of the two images displayed are suitably in colour and have, for example, a resolution of approximately 800 pixels horizontally and approximately 600 pixels vertically for each of the three primary colours RGB (red, green and blue), each image thus being able to contain three times the number of pixels, that is approximately 1.4 million pixels. The cameras and monitors that are currently available on the market do not yet have such a high resolution, however, for which reason the image quality that can be used is still limited by these. As mentioned, the properties of the image can be changed by the user by means of suitable operating controls 23 on the driver unit 9 or by means of, for example, voice control.

For stereoscopic vision, the image signals generated by the endoscope 4 and the camera 7 can be transmitted to the two display modules 13 and 14 in various ways. One possibility is to use separate leads, one lead transmitting the right-hand image and the other lead transmitting the left-hand image. Another possibility is to use a shared lead almost right up to the display units and to transmit right-hand and left-hand images alternately via this lead, and only to divide the signal up into two leads, one for each display unit, close to the display units. This latter, preferred possibility reduces the need for leads.

A device according to the invention can, of course, be used for other purposes than for surgery. One such possible area of application is, for example, for inspecting or working in areas in mechanical equipment that are difficult to access.

In order to ensure good functioning of the equipment, it is expedient that the computer 8 monitors the equipment by carrying out regular function controls automatically, at least when the equipment is put into use and also regularly during use.

Figure 7:
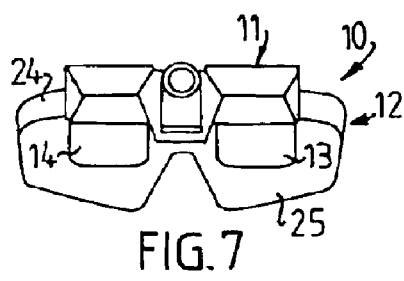
FIG. 7 shows a front view of an embodiment of a display according to the invention.
Figure 8:
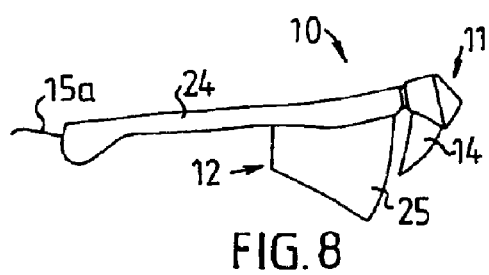
FIG. 8 shows a side view of the display in FIG. 7.
Figure 9:
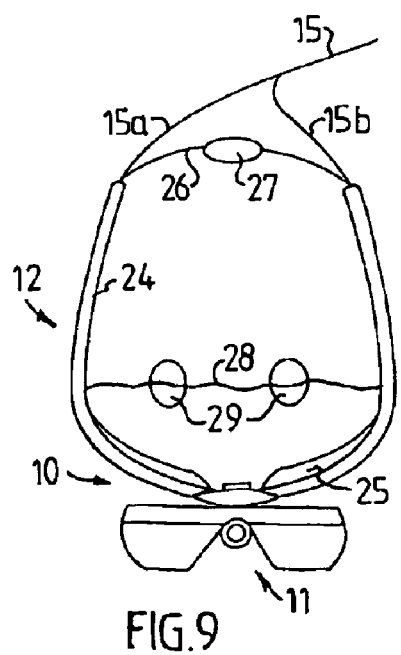
FIG. 9 shows a view from above of the display in FIGS. 7 and 8.

A further embodiment of a display 10 according to the invention is shown in greater detail in FIGS. 7–9. As shown, the holder 12 has here been designed to enclose the user's face and eyes with a frame 24 and a visor 25, but still to give the user good vision to the side of the display unit 11 and above and below it. The visor 25 can suitably be mounted on the frame 24 in such a way that it can be removed, for example for cleaning. As in the previously described embodiment, the display unit 11 is mounted on the holder 12 in such a way that it can be removed, and can be connected electrically to the holder 12 via connectors (not shown), which holder is in turn designed to be connected to the driver unit 9, suitably via a lead 15. This lead 15 is, according to FIG. 9, suitably divided into two branches 15a and 15b at the holder 12, each of which runs through an arm of the holder 12, up to the respective display unit 13, 14.

In order to make the display 10 lighter to wear, the two arms of the frame 24 are connected at the back by a strap 26 on which there is a pad 27 designed to be in contact with the back of the user's head, the length of the strap 26 and the position of the pad 27 being suitably adjustable to fit the user in question. A suitable position for the pad 27 when in use is shown in FIG. 6. In order to relieve the strain on the back of the user's head and on his back, there can suitably be a strain-taker 28, for example in the form of a clip or the like, that can be clipped onto the user's clothing in order to reduce the load on the back of the user's head from the lead 15.

In order to make the display 10 even lighter to wear by relieving the pressure on the user's nose, it can, as shown in FIG. 9, be provided with a strap 28 attached on both sides of the front part of the frame 24, which strap is intended to be stretched over the crown of the user's head and to be supported by two pads 29 placed a distance apart. By adjusting the length of the strap 28, the pressure on the user's nose can be relieved to the required extent, and as the pads 29 are positioned a certain distance apart, pressure is avoided on the sensitive central part of the skull.

A perception of depth in the image which is restful for the viewer is obtained according to the invention by the focal plane being placed essentially centrally in the image. By this means, objects can be perceived to lie at, in front of or behind the focal plane in a natural way.

It has been proposed above that the display unit 11 can be adjusted to a user's interpupillary distance d by making the two display modules 13 and 14 moveable in relation to each other. Another advantageous possibility is to manufacture the display unit 11 in a small number of standard sizes for the interpupillary distance d, for example in three different standard sizes. This would result in a simplification of the display unit 11, while at the same time a large majority of users would be able to use one of these standard sizes. In association with this, to make possible individual fine-tuning of the interpupillary distance, it can advantageously be arranged that the image in each of the two display modules 13 and 14 can be moved slightly in a horizontal and vertical direction by electronic means. Suitable values of such movement can, for example, be 8 pixels in each direction sideways and, for example, 6 pixels in each direction up or down, starting from a normal position.

In order to be able to free up the user's field of vision completely, the display unit 11 can be made so that it flips up, so that, if required, it can be flipped up away from the user's field of vision.

The focal plane of the image is located, as mentioned above, at a suitable distance from the user for the task in hand. For special tasks, the distance can be increased right up to approximately 2 metres.

For a user who wears spectacles, optical adjustment of the display 10, as mentioned, can be carried out by the holder 12 with its visor being provided with an optical adjustment. It is, however, also possible instead to use the user's own spectacles as the mounting for the display unit 11.

What is claimed is:

1. A device for displaying an image, comprising:
   a holder that is arranged and adapted to be worn on a face of a user and that has a bridge section that extends across the user's face above the user's eyes in use;
   a frame that is removably attachable to said bridge section substantially parallel to said bridge section and that is arranged and adapted to be above a field of view of a user in use;
   first and second image screens that are each within said frame spaced apart from each other by a first distance;
   first and second image screen light sources that are each within said frame adjacent to a respective one of said first and second image screens; and
   first and second prisms that each depend from said frame into a field of view of a user and that are spaced apart from each other by a second distance, said first and second prisms obscuring ambient light while allowing a user to receive ambient light from below and beside said prisms,
   said first and second image screens projecting respective images into corresponding ones of said first and second prisms, each of the respective images having a dark border therearound, wherein the respective images together form a three-dimensional image for a user.

2. The device of claim 1, wherein the second distance is adjustable.

3. The device of claim 1, wherein centers of said images are approximately 2–12° below a horizontal plane through a user'eyes during use of the device.

4. The device of claim 1, wherein diagonals from one side to another side of each of said prisms subtend an arc of no more than 50° of a field of vision of a user.

5. The device of claim 1, wherein diagonals across each of said images subtend an arc of at least 15° of a field of vision of a user.

6. The device of claim 1, wherein said images are round.

7. The device of claim 1, wherein the first distance generally corresponds to a distance between a user's eyes.

8. The device of claim 1, wherein said holder comprises a pair of lenses that depend from said bridge section into a field of vision of a user.

9. A Method of displaying a image, the method comprising the steps of:
   arranging a holder on a face of a user, the holder having a bridge section that extends across the user'face above the user's eyes in use;
   removably attaching a frame to the bridge section substantially parallel to the bridge section, the frame being above a field of view of a user in use;
   providing first and second image screens within the frame spaced apart from each other by a first distance;
   providing first and second image screen light sources that are each within the frame adjacent to a respective one of the first and second image screens; and
   providing first and second prisms that each depend from the frame into a field of view of a user and that are spaced apart from each other by a second distance, the first and second prisms obscuring ambient light while allowing a user to receive ambient light from below and beside the prisms, projecting respective images from the first and second image screens into corresponding ones of the first and second prisms, each of the respective images having a dark border therearound, wherein the respective images together form a three-dimensional image for a user.

10. The method of claim 9, further comprising the steps of adjusting the second distance.

11. The method of claim 9, wherein the images are round.

* * * * *